United States Patent [19]

Wittenhorst

[11] 4,380,505
[45] Apr. 19, 1983

[54] APPARATUS FOR PRODUCING AEROSOL PRODUCT

[75] Inventor: Augustinus J. M. Wittenhorst, Westerburg, Fed. Rep. of Germany

[73] Assignee: von Treu AG, Zug, Switzerland

[21] Appl. No.: 202,448

[22] PCT Filed: Nov. 10, 1979

[86] PCT No.: PCT/DE79/00136

§ 371 Date: Jul. 11, 1980

§ 102(e) Date: Jul. 10, 1980

[87] PCT Pub. No.: WO80/00973

PCT Pub. Date: May 15, 1980

[30] Foreign Application Priority Data

Nov. 11, 1978 [DE] Fed. Rep. of Germany ....... 2849074

[51] Int. Cl.$^3$ ............................ B01F 5/00; B01J 13/00
[52] U.S. Cl. .................................. 252/359 R; 53/470;
252/305; 424/43
[58] Field of Search ............. 252/305, 359 R; 424/45,
424/47; 53/470

[56] References Cited

U.S. PATENT DOCUMENTS

| | | | |
|---|---|---|---|
| 3,102,101 | 8/1963 | Hawley et al. | 252/305 |
| 3,134,720 | 5/1964 | Green et al. | 252/305 X |
| 3,155,574 | 11/1964 | Silson et al. | 424/45 |
| 3,330,773 | 7/1967 | DeHart, Jr. | 252/305 X |
| 3,361,679 | 1/1968 | Paulus | 252/305 |

FOREIGN PATENT DOCUMENTS

| | | | |
|---|---|---|---|
| 1170909 | 5/1964 | Fed. Rep. of Germany | 252/305 |
| 2131668 | 1/1972 | Fed. Rep. of Germany | 252/305 |

*Primary Examiner*—Richard D. Lovering
*Attorney, Agent, or Firm*—Cushman, Darby & Cushman

[57] ABSTRACT

The aerosol product, for example a cosmetic or pharmaceutical preparation, contains an active agent, a propelling agent and a solvent; with a view to protect the environment and the users the propelling agent is comprised exclusively of, helium, neon, argon, krypton or mixtures of these gases. A percentage of at least 80% by weight of argon with respect to the total weight of the propelling agent has proved to be particularly interesting. The method consist mainly in contacting the active agent and the solvent into an autoclave, introducing a compressed noble gas in a predetermined amount and collecting the mixture obtained. The mixing process may be repeated in other autoclaves with different noble gases. The device comprises mixtures (1,2;3) for storing the active agent and the solvent connected, as well as a pressure accumulator (a) for noble gases, to an autoclave (12) on which an outlet connection (14) is fixed, above the ground. Several autoclaves (15, 18) may be provided as well as a filter having the shape of a candle (22, 10a), arranged after the last autoclave (18) and/or before the first autoclave (12).

3 Claims, 1 Drawing Figure

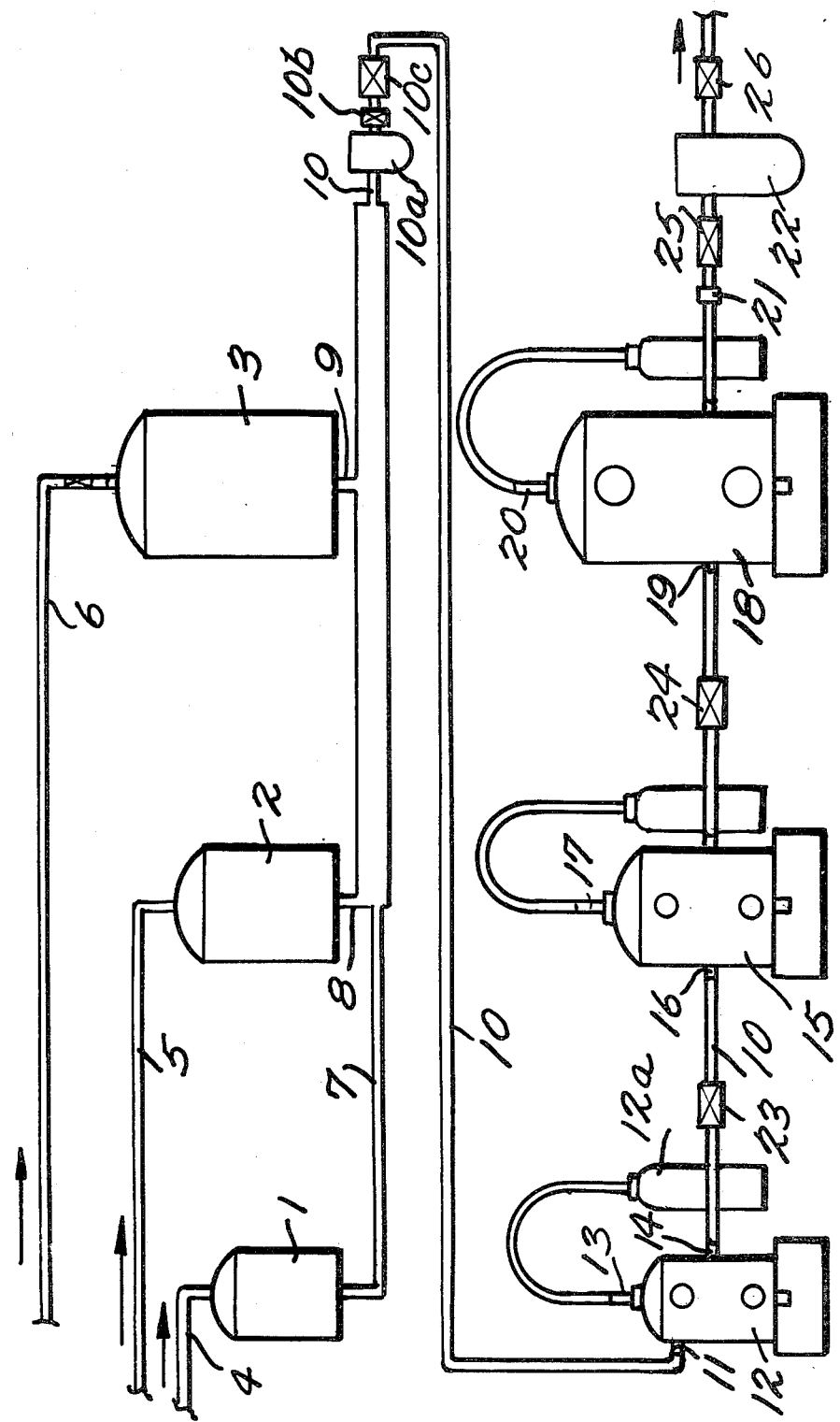

APPARATUS FOR PRODUCING AEROSOL PRODUCT

TECHNICAL FIELD

The invention relates to an aerosol product consisting of an active substance, propellant and solvent. Furthermore, the invention concerns a process for the production of an aerosol product as well as an apparatus for carrying out the process.

STATUS OF THE PRIOR ART

Aerosol products with different propellants have been known. Since the propellants become volatile upon atomization and at the same time may easily reach up to open spaces of combustion, it is generally demanded of them that their combustibility be lowered.

A known example for such propellants is chlorine fluorine hydrocarbons. However, their use does not seem to be quite harmless, since there at least exists the possibility that in the case of a continuous and larger expulsion into the atmosphere of the earth, an attack on the ozone belt surrounding the earth takes place which is of significance for the absorption of UV radiation.

Also propellants free of chlorine fluorohydrocarbons have been known (cf. German OS No. 2 741 882), namely with 65 to 85% by weight of 1,1,1-trichloroethane, dichloro methane or mixtures of these, 14 to 32% by weight of butane, isobutane, propane or mixtures thereof and approximately 0.5 to 5.3% by weight of carbon dioxide.

The high portion of 1,1,1-trichloroethane for many fields of application is a disadvantage in that case. For one thing, when sprayed into an open flame, as it occurs regularly in the case of laboratory experiments (flame tests, etc.) or also unintentionally in practical use, these components are subject to decomposition reactions, whereby among others hydrochloric acid may develop and for another thing, it is also risky even without any decomposition taking place, whenever a consumer comes into direct contact with those components, especially if he also inhales them along with others. This comes into consideration mainly in the case of aerosol products in the field of pharmaceutics but also in the case of numerous other aerosol products, since their liberation practically always takes place in the immediate vicinity of the consumer.

DESCRIPTION OF THE INVENTION

This is where the invention starts. It is based on the task of describing an aerosol product from which these dangers no longer emanate. Thus, the areosol product as far as its propellant is concerned, is to be distinguished by a decrease combustibility as well as by a neutral behavior concerning the environment, as well as concerning the immediate health of the consumer. Furthermore, the invention is to describe a process for the production of such an aerosol product as well as an aparatus to carry out the process.

The task is solved in the case of an aerosol product consisting of an active substance, a propellant and a solvent, in a surprisingly simple and at the same time effective manner by the fact that the propellant consists exclusively of helium, neon, argon, krypton or mixtures thereof.

This is true both for powdered sprays, foam sprays, as well as above all wetting sprays. The number of noble gases cited depends for one thing on their cost and for another thing on their physical properties.

From the German Pat. No. 1 170 909 self-propellant mixtures have been known which as propellants contain an inert gas and a halogenated methane. At the same time, the inert gas consists of a mixture of sulfuric hexafluoride and an inert, noncombustible gas, for example, also argon, helium or neon.

The German OS No. 21 31 668 concerns an anaerobic agent, especially adhesives in aerosol form, setting especially in the presence of oxygen. Beside the "anaerobic agent", there is an inert gas and oxygen present in the containers under pressure. Beside its chemical functions, the oxygen at the same time also acts as a propellant. Helium, neon and argon are mentioned among others also as inert gases.

From none of the previously mentioned printed documents does the use of noble gases as sole propellant for aerosols become clear.

Noble gases are absolutely incombustible and thus they are superior to propellants hitherto. Furthermore, they constitute no danger for the atmosphere of the earth but they are altogether to be classified as compatible with the environment. As is well known, they are obtained, indeed, in a purely physical way from the environmental air, so that their later liberation signifies no contamination or impairment of the environment, but merely a return to their origin.

Further advantages are that their use is probably harmless from a dermatological and toxicological point of view for the human being as well as for animals; finally, the human being inhales and exhales about 20 liter of argon daily together with the respiratory air.

Noble gas has the advantage of acting without intoxicating effect, especially for aerosol products in the field of pharmaceutics. As is well known, aerosol products which contain chloro fluoride hydrocarbons as propellants may have an intoxicating effect. This effect is also used by numerous labile patients for the purpose of getting intentionally intoxicated. Quite a few patients have come thereby into a dependence on such aerosol products which is expressed frequently also by the fact that already corresponding medical weaning cures are made and are advertised in newspaper advertisements.

The significance of the invention for aerosol products in the field of pharmaceutics may be illuminated further by the fact that presently several dozens of medical preparations are sold in aerosol form in a regular drugstore, among them so-called nitro sprays (as prescribed in the case of contraction of the coronary vessels of the heart), asthma sprays, throat and mouth sprays, for the treatment of eczemae, wound sprays and sprays for dressings of wounds, etc.

Let us also mention that noble gases probably also have a sterilizing, bacteria killing effect, which in any case is desirable.

Furthermore, noble gases have the advantage of being odorless and therefore they are suitable particularly also as aerosol products in the field of cosmetics.

In addition, noble gases lead to an excellent spray behavior in the case of aerosol products. Owing to their good capacity for dissolution in liquids, sufficient quantities of propellants may easily be dissolved in liquid active substances or the solvents for active substances and a favorable adjustment of the pressure conditions may be achieved, i.e., a more or less constant operating pressure and a uniform distribution (fine atomization).

Finally, the rise in pressure by increase of temperature is low in the case of noble gases, which additionally represents a particular safety factor.

Effectively, the propellant is a mixture of the above mentioned noble gases.

It is particularly advantageous whenever the propellant is a mixture of noble gases with a share of argon of at least 80% by weight related to the total weight of the propellant.

For the production of an aerosol product according to the invention, the active substance and the solvent are brought together under pressure according to a further proposal of the invention, are charged overhead to a pressure container and seeped in it. At the same time, a noble gas compressed overhead is introduced into the pressure tank and is added by doses to the active substance-solvent mixture. Subsequently, the mixture that develops is collected and is fed to a bottling plant. In this way, the aerosol product may be enriched to a sufficient degree with noble gas.

Advantageously, the active substance-solvent mixture is charged to further pressure tanks and processed as before. Preferably, various noble gases are introduced into the pressure tanks.

The apparatus according to the invention is characterized by a mixing vessel for the storage of active substance, a mixing vessel for the storage of solvent, whereby the mixing vessels have feed lines separated from one another and are provided with discharge lines which converge to a common conveying line, furthermore by a pressure tank with an inlet connection overhead to which the common conveying line is connected, a further inlet connection overhead to which a pressure storage for noble gas is connected as well as an escape connection which is disposed at a distance from the floor of the pressure tank.

Advantageously, additional pressure tanks are provided.

In a further development of the idea of the invention, a filtering candle has been provided behind the last pressure tank and/or in front of the first pressure tank.

BRIEF DESCRIPTION OF THE DRAWING

The invention is to be explained further subsequently in connection with the drawing. The only FIGURE shows an apparatus according to the invention in a diagrammatic simplification.

According to the FIGURE, the apparatus consists of a mixing vessel 1 for an active substance and a mixing vessel 2 for another active substance, further of a mixing vessel 3 for a solvent. Separate feed lines 4, 5, 6 lead to the individual mixing vessels 1, 2, 3 which always have an agitating mechanism. Discharge lines 7, 8,9 start off from the mixing vessels 1, 2, 3 which converge into a common conveying line 10. The latter has a filter candle 10a, a conveying pump 10b and a locking slide 10c. The conveying line 10 is connected furthermore to an inlet connection 11 of a pressure vessel 12. The inlet connection 11 at the same time is disposed overhead of the pressure vessel 12. Likewise overhead, an additional inlet connection 13 is disposed on the pressure vessel 12 to which a pressure tank (in this case a pressure flask) 12a for a noble gas has been connected.

At a distance from its floor, the pressure vessel has a discharge connection 14. Another section of the conveying line 10 is connected thereto and leads to a further pressure vessel 15 which, in turn, has again a connection 16 for the arriving mixture and an inlet connection 17 for the noble gas to be added by doses. Analogously, a further step with a pressure vessel 18 and an inlet connection 19, 20 follows. The pressure vessels 12, 15, 18 in this case are developed as pressure filter vessels.

The last filter container 18 is again followed by a section of the conveying line 10. An excess pressure valve 21 as well as a filter candle 22 are inserted in the latter. The latter contains a transparent outside housing and at the same time it makes possible a visible control before the mixture obtained will reach a filling plant not shown here. As can be seen furthermore, before and behind each pressure vessel 12, 15, 18, a closing slide has been provided, namely the closing slide 10c already mentioned as well as the additional closing slides 23, 24 and 25. Finally, one more closing slide is attached also behind the filter candle 22 which has been designated here by 26.

The apparatus of the invention operates as follows: The active substances or the solvents flow via their pertinent discharge lines 7, 8 or 9 into the common conveying line 10. There, they are mixed under pressure. The active substance-solvent mixture then reaches the pressure container 12 where it enters overhead and seeps. At the same time krypton is likewise introduced overhead and added by doses to the mixture.

The mixture obtained thus subsequently reaches the pressure vessel 15 where an enrichment with helium takes place in a similar manner. Thereupon, that mixture reaches the pressure vessel 18 where an even greater enrichment with argon takes place, namely with at least 80% by weight related to the total weight of the propellant. After passing through the filter candle 22, the aerosol product according to the invention reaches a filling plant for bottling.

I claim:

1. Apparatus suitable for the production of an aerosol product consisting of active substance, propellant and solvent wherein the propellant consists exclusively of a noble gas which is helium, neon, argon, krypton or mixtures thereof by a process comprising bringing together the active substance and the solvent under pressure, charging overhead to a pressure vessel and seeping therein, while at the same time introducing into the pressure vessel a compressed noble gas and adding the noble gas by doses to the active substance-solvent mixture and subsequently collecting the newly developed mixture and feeding it to a bottling plant, said apparatus comprising a mixing vessel (1, 2) for the storage of active substance, a mixing vessel (3) for the storage of solvent, whereby the mixing vessels (1, 2; 3) have feed lines (4, 5; 6) separated from one another and are provided with discharge lines (7, 8; 9) which converge to a common conveying line (10), furthermore characterized by a pressure tank (12) with an inlet connection (11) overhead, which is connected to the common conveying line (10), an additional inlet connection (13) overhead, to which a compression tank (12a) for noble gas has been connected as well as a discharge connection (14) which is disposed at a distance from the bottom of the pressure vessel (12).

2. Apparatus as in claim 1, characterized in that additional pressure vessels (15, 18) have been provided.

3. Apparatus as in claim 1 or 2, characterized in that behind the last pressure vessel (18) and/or before the first pressure vessel (12) a filter candle (22, 10a) has been provided.

* * * * *